US006274143B1

(12) United States Patent
Chatterjee et al.

(10) Patent No.: US 6,274,143 B1
(45) Date of Patent: Aug. 14, 2001

(54) METHODS OF DELAYING DEVELOPMENT OF HMFG-ASSOCIATED TUMORS USING ANTI-IDIOTYPE ANTIBODY 11D10

(76) Inventors: Malaya Chatterjee, 2400 The Woods La., Lexington, KY (US) 40502; Kenneth A. Foon, 800 Rose St., Lexington, KY (US) 40536

(*) Notice: Subject to any disclaimer, the term of this patent is extended or adjusted under 35 U.S.C. 154(b) by 0 days.

(21) Appl. No.: 09/096,244

(22) Filed: Jun. 11, 1998

Related U.S. Application Data

(60) Provisional application No. 60/049,540, filed on Jun. 13, 1997.

(51) Int. Cl.[7] .................. A61K 39/395; A61K 39/40; C07K 16/00
(52) U.S. Cl. ...................... 424/155.1; 530/387.2; 424/131.1; 424/138.1; 424/139.1; 424/155.1; 424/156.1; 424/143.1; 424/174.1
(58) Field of Search .............. 530/387.2; 424/131.1, 424/138.1, 139.1, 155.1, 156.1, 143.1, 174.1

(56) References Cited

U.S. PATENT DOCUMENTS

| 4,436,728 | 3/1984 | Ribi et al. . |
| 4,726,947 | 2/1988 | Shimada et al. . |
| 5,057,540 | 10/1991 | Kensil et al. . |
| 5,077,284 | 12/1991 | Loria et al. . |

FOREIGN PATENT DOCUMENTS

| WO 89/07268 | 8/1989 | (WO) . |
| WO 91/11465 | 8/1991 | (WO) . |
| WO 91/16924 | 11/1991 | (WO) . |
| WO 92/16231 | 10/1992 | (WO) . |
| WO 94/02608 | 2/1994 | (WO) . |
| WO 97/22699 | 6/1997 | (WO) . |

OTHER PUBLICATIONS

Johnson et al Cancer Treatment review vol. 2, 1–31, 1975.*
Pervin, S. et al., "Proliferation of T–cells from colon cancer patients by peptides based on the structure of an anti–idiotype antibody mimicking CEA" *Proc. Am. Assoc. Cancer Res.* 37:473 Abstract No. 3231 (1997).
Tripathi P. K. et al., "Anti–idiotype–cytokine fusion protein for breast cancer therapy" *Proc. Am. Assoc. Cancer Res.* 38:84 Abstract No. 563 (1997).
Bhattacharya–Chatterjee et al., "Anti–idiotype antibodies as potential therapeutic agents for human breast cancer" (1994) *Antigen and Antibody Mole. Eng. Breast Cancer Diagnosis and Treatment*, (R.L. Ceriani, Ed.) 139–148.
Ceriani et al., "Surface differentiation antigens of human mammary epithelial cells carried on the human milk fat globule" (1977) *Proc. Natl. Acad. Sci. USA* 74:582–586.
Ceriani et al., "Characterization of cell surface antigens of human mammary epithelial cells with monoclonal antibodies prepared against human milk fat globule" (1983) *Somatic Cell Genet.* 9(4):415–427.

Ceriani et al., "Immunotherapeutic preclinical evaluation of anti–human milk fat globule MoAbs Mc5 and BrE–1" (1990) *Antibody Immunoconjugates and Radiopharmaceuticals* 3(3):181–198.

Chakraborty et al., "Induction of human breast cancer–specific antibody responses in cynomolgus monkeys by a murine monoclonal anti–idiotype antibody" (1995) *Cancer Res.* 55:1525–1530.

Chakraborty et al., "Immune responses in advanced breast cancer patients treated with an anti–idiotype antibody vaccine" (1997) *Proc. Am. Assoc. Cancer Res.* 38:616 Abstract No. 4139.

Charaborty et al., "Induction of human breast cancer–specific antibody response in cynomolgus monkeys by a murine monoclonal anti–idiotype antibody" (1994) *Proc. Am. Assoc. Cancer Res.* 35:497 Abstract No. 2963.

Chatterjee et al., Antiidiotype (Ab2) vaccine therapy for cutaneous T–cell lymphoma (1993) *Ann. N.Y. Acad. Sci.* 690:376–377.

Cheresh et al., "Disialoganlioside GD3 on human melanoma serves as a relevant target antigen for monoclonal antibody–mediated tumor cytolysis" (1985) *Proc. Natl. Acad. Sci. USA* 85:5155–5159.

Cheresh et al., "Biosynthesis and expression of the disialoganglioside $G_{D3}$, a relevant target antigen on small cell lung carcinoma for monoclonal antibody–mediated cytolysis" (1986) *Cancer Res.* 46:5112–5118.

Herlyn, D.M. and Koprowski, H., "Monoclonal anticolon carcinoma antibodies in complement–dependent cytotoxicity" (1981) *Int. J. Cancer* 27:769–774.

Herlyn et al., "Anti–idiotype immunization of cancer patients: Modulation of the immune response" (1987) *Proc. Natl. Acad. Sci. USA* 84:8055–8059.

Honjo et al., "Cloning and complete nucleotide sequence of mouse immunoglobulin γ1 chain gene" (1979) *Cell* 18:559–568.

Jerne, N.K., "Towards a network theory of the immune system" (1974) *Ann. Immunol.* 125:373–389.

Khazaeli et al., "Phase I trial of multiple large doses of murine monoclonal antibody CO17–1A" (1988) *J. Natl. Cancer Inst.* 80:937–942.

(List continued on next page.)

Primary Examiner—Anthony C. Caputa
Assistant Examiner—Mau Tran
(74) Attorney, Agent, or Firm—Morrison & Foerster LLP

(57) ABSTRACT

The present invention provides methods of delaying development of HMFG-associated tumors using the anti-idiotype antibody 11D10, particularly in high-risk individuals having low tumor burden.

24 Claims, 4 Drawing Sheets

OTHER PUBLICATIONS

Lindenmann, J., "Speculations on idiotypes and homobodies" (1973) *Ann. Immunol. 124*:171–184.

McBride, W.H. and Howie, S.E.M., "Induction of tolerance to a murine fibrosarcoma in two zones of dosage—The involvement of suppressor cells" (1986) *Br. J. Cancer 53*:707–711.

Mittleman et al., "Human high molecular weight melanoma–associated antigen (HMW–MAA) mimicry by mouse anti–idiotypic monoclonal antibody MK2–23: Induction of humoral anti–HMW–MAA immunity and prolongation of survival in patients with stage IV melanoma" (1992) *Proc. Natl. Acad. Sci. USA 89*:466–470.

Mukerjee et al., "Generation of anti–anti–idiotype antibodies (Ab3) that recognize human breast cancer" (1992) *FASEB J. 6*(5):A2059 Abstract No. 6505.

Mukerjee et al., "Syngeneic monoclonal anti–idiotype antibodies against a monoclonal antibody to human breast cancer–associated antigen" (1992) *FASEB J. 6*:A1713 Abstract No. 7792.

Peterson et al., "Biochemical and histological characterization of antigens preferentially expressed on the surface and cytoplasm of breast carcinoma cells identified by monoclonal antibodies against the human milk fat globule" (1990) *Hybridoma 9*(3):221–235.

Solin, M–L. and Kaartinen, M., "Immunoglobulin constant kappa gene alleles in twelve strains of mice" (1993) *Immunogenetics 37*:401–407.

Stevens et al., "Generation of tumor–specific CTLs from melanoma patients by using peripheral blood stimulated with allogeneic melanoma tumor cell lines" (1995) *J. Immunol. 154*(2):762–771.

Takahashi et al., "Induction of $CD8^+$ cytotoxic T cells by immunization with purified HIV–1 envelope protein in ISCOMs" (1990) *Nature 344*:873–875.

* cited by examiner

Figure 1

```
      M    G    A    P    A    Q    I    L    G    F
     ATG  GGG  GCC  CCT  GCT  CAG  ATT  CTT  GGG  TTC

L    L    L    L    F    P    G    T    R    C
     TTG  TTG  CTC  TTG  TTT  CCA  GGT  ACC  AGA  TGT
     (leader, -20-1)

D    I    Q    M    T    Q    S    P    S    S
     GAC  ATC  CAG  ATG  ACC  CAG  TCT  CCA  TCC  TCC
      L    S    A    S    L    G    Q    R    V    S
     TTA  TCT  GCC  TCT  CTG  GGA  CAA  AGA  GTC  AGT
      L    T    C
     CTC  ACT  TGT   (fr.1, 1-23)

R    A    S    Q    D    I    G    I    N    L
     CGG  GCA  AGT  CAG  GAC  ATT  GGT  ATT  AAC  TTA
      H
     CAT   (cdr1, 24-34)

T    L    Q    Q    E    P    D    G    T    I
     TGG  CTT  CAG  CAG  GAA  CCA  GAT  GGA  ACT  ATT
      K    R    L    I    Y
     AAA  CGC  CTG  ATC  TAC   (fr2., 35-49)

A    T    S    S    L    G    S
     GCC  ACA  TCC  AGT  TTA  GGT  TCT   (cdr2, 50-56)

G    V    P    K    R    F    S    G    S    R
     GGT  GTC  CCC  AAA  AGG  TTC  AGT  GGC  AGT  AGG
      S    G    S    D    Y    S    L    T    I    S
     TCT  GGG  TCA  GAT  TAT  TCT  CTC  ACC  ATC  AGC
      S    L    E    S    E    D    F    V    A    Y
     AGC  CTT  GAG  TCT  GAA  GAT  TTT  GTA  GCC  TAT
      Y    C
     TAC  TGT   (fr3, 57-88)

L    Q    Y    A    S    S    P    Y    T
     CTA  CAA  TAT  GCT  AGT  TCT  CCG  TAC  ACG
     (cdr3, 89-97)

F    G    G    G    T    K    L    E    I    K
     TTC  GGA  GGG  GGG  ACC  AAG  CTG  GAA  ATA  AAA
     (fr4, 98-107)

R    A    D    A    A    P    T    V    S    I
     CGG  GCT  GAT  GCT  GCA  CCA  ACT  GTA  TCC  ATC
      F    P    P    S    S    K    L    G
     TTC  CCA  CCA  TCC  AGT  AAG  CTT  GGG
```

Figure 2

```
      M   E   C   S   W   V   F   L   F   L   L   S   I   T   T   G   V
     ATG GAA TGC AGC TGG GTC TTT CTC TTC CTC CTG TCA ATA ACT ACA GGT GTC
     Met Glu Cys Ser Trp Val Phe Leu Phe Leu Leu Ser Ile Thr Thr Gly Val

H   S
     CAC TCC
     His Ser    (leader)

Q   A   Y   L   Q   Q   S   G   A   E   L   V   R   S
     CAG GCT TAT CTA CAG CAG TCT GGG GCT GAG CTG GTG AGG TCT
     Gln Ala Tyr Leu Gln Gln Ser Gly Ala Glu Leu Val arg Ser G   A   S   V   K   M   S   C   K   A   S   G   Y   T   L   T
     GGG GCC TCA GTG AAG ATG TCC TGC AAG GCT TCT GGC TAC ACA TTG ACC
     Gly Ala Ser Val Lys Met Ser Cys Lys Ala Ser Gly Tyr Thr leu Thr
     (1-30, Fr.#1)

S   Y   N   M   H
     AGT TAC AAT ATG CAC
     Ser Tyr Asn Met His    (31-35, CDR 1)

W   V   K   Q   T   P   G   Q   G   L   E   W   I   G
     TGG GTA AAG CAG ACA CCT GGA CAG GGC CTG GAA TGG ATT GGA
     Trp Val Lys Gln Thr Pro Gly Gln Gly Leu Glu Trp Ile Gly (36-49, Fr. #2)

N   I   F   P   G   N   G   D   T   Y   Y   N   Q   K   F   K   G
     AAT ATT TTT CCT GGA AAT GGT GAT ACT TAC TAC AAT CAG AAG TTT AAG GGC
     Asn Ile Phe Pro Gly Asn Gly Asp Thr Tyr Tyr Asn Gln Lys Phe Lys Gly
     (50-66, CDR 2)

K   A   S   L   T   A   D   T   S   S   S   T   A   Y   M   Q
     AAG GCC TCA TTG ACT GCA GAC ACA TCC TCC AGC ACA GCC TAC ATG CAG
     Lys Ala Ser Leu Thr Ala Asp Thr Ser Ser Ser Thr Ala Tyr Met Gln

I   S   S   L   T   S   E   D   S   A   V   Y   F   C   A   R
     ATC AGC AGC CTG ACA TCT GAA GAC TCT GCG GTC TAT TTC TGT GCA AGA
     Ile Ser Ser Leu Thr Ser Glu Asp Ser Ala Val Tyr Phe Cys Ala Arg (67-98, Fr.# 3)

G   N   W   E   G   A   L   D   Y
     GGG AAC TGG GAG GGT GCT CTG GAC TAC
     Gly Asn Trp Glu Gly Ala Leu Asp Tyr (99-107, CDR 3)

W   G   Q   G   T   S   V   T   V   S   S
     TGG GGT CAA GGA ACC TCA GTC ACC GTC TCC TCA
     Trp Gly Gln Gly Thr Ser Val Thr Val Ser Ser (108-118, Fr. # 4)
      A   K   T   T   P   P   P   V   Y   P   L   V   P   G   S   L
     GCC AAA ACG ACA CCC CCA CCC GTC TAT CCA CTG GTC CCT GGA AGC TTG GG
     Ala Lys Thr Thr Pro Pro Pro Val Tyr Pro Leu Val Pro Gly Ser Leu (constant region)
```

Figure 3A

DIQMTQSPSSLSASLGQRVSLTC — Framework #1, 1–23

RASQDIGINLH — CDR-1, 24–34

TLQQEPDGTIKRLIY — Framework #2, 35–49

ATSSLGS — CDR-2, 50–56

GVPKRFSGSRSGSDYSLTISSLESEDFVAYYC — Framework #3, 57–88

LQYASSPYT — CDR-3, 89–97

FGGGTKLEIK — Framework #4, 98–107

Figure 3B

QAYLQQSGAELVRSGASVKMSCKASGYTLT — Framework #1, 1–30

SYNMH — CDR-1, 31–35

WVKQTPGQGLEWIG — Framework #2, 36–49

NIFPGNGDTYYNQKFKG — CDR-2, 50–66

KASLTADTSSSTAYMQISSLTSEDSAVYFCAR — Framework #3, 67–98

GNWEGALDY — CDR-3, 99–107

WGQGTSVTVSS — Framework #4, 108–118

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 435 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 1..435

(ix) FEATURE:
       (A) NAME/KEY: mat_peptide
       (B) LOCATION: 61

(xi) SEQUENCE DESCRIPTION: SEQ ID NO:1:

```
ATG GGG GCC CCT GCT CAG ATT CTT GGG TTC TTG TTG CTC TTG TTT CCA      48
Met Gly Ala Pro Ala Gln Ile Leu Gly Phe Leu Leu Leu Leu Phe Pro
-20             -15                 -10                  -5

GGT ACC AGA TGT GAC ATC CAG ATG ACC CAG TCT CCA TCC TCC TTA TCT      96
Gly Thr Arg Cys Asp Ile Gln Met Thr Gln Ser Pro Ser Ser Leu Ser
                 1                   5                  10

GCC TCT CTG GGA CAA AGA GTC AGT CTC ACT TGT CGG GCA AGT CAG GAC     144
Ala Ser Leu Gly Gln Arg Val Ser Leu Thr Cys Arg Ala Ser Gln Asp
         15                  20                  25

ATT GGT ATT AAC TTA CAT TGG CTT CAG CAG GAA CCA GAT GGA ACT ATT     192
Ile Gly Ile Asn Leu His Trp Leu Gln Gln Glu Pro Asp Gly Thr Ile
         30                  35                  40

AAA CGC CTG ATC TAC GCC ACA TCC AGT TTA GGT TCT GGT GTC CCC AAA     240
Lys Arg Leu Ile Tyr Ala Thr Ser Ser Leu Gly Ser Gly Val Pro Lys
45                  50                  55                  60

AGG TTC AGT GGC AGT AGG TCT GGG TCA GAT TAT TCT CTC ACC ATC AGC     288
Arg Phe Ser Gly Ser Arg Ser Gly Ser Asp Tyr Ser Leu Thr Ile Ser
                 65                  70                  75

AGC CTT GAG TCT GAA GAT TTT GTA GCC TAT TAC TGT CTA CAA TAT GCT     336
Ser Leu Glu Ser Glu Asp Phe Val Ala Tyr Tyr Cys Leu Gln Tyr Ala
                 80                  85                  90

AGT TCT CCG TAC ACG TTC GGA GGG GGG ACC AAG CTG GAA ATA AAA CGG     384
Ser Ser Pro Tyr Thr Phe Gly Gly Gly Thr Lys Leu Glu Ile Lys Arg
         95                  100                 105

GCT GAT GCT GCA CCA ACT GTA TCC ATC TTC CCA CCA TCC AGT AAG CTT     432
Ala Asp Ala Ala Pro Thr Val Ser Ile Phe Pro Pro Ser Ser Lys Leu
         110                 115                 120

GGG                                                                  435
Gly
125
```

(2) INFORMATION FOR SEQ ID NO:2:

(i) SEQUENCE CHARACTERISTICS:
       (A) LENGTH: 145 amino acids
       (B) TYPE: amino acid
       (D) TOPOLOGY: linear (ii) MOLECULE TYPE: protein (xi) SEQUENCE DESCRIPTION: SEQ ID NO:2:

```
Met Gly Ala Pro Ala Gln Ile Leu Gly Phe Leu Leu Leu Phe Pro
-20                 -15                 -10                  -5

Gly Thr Arg Cys Asp Ile Gln Met Thr Gln Ser Pro Ser Ser Leu Ser
                  1               5                   10

Ala Ser Leu Gly Gln Arg Val Ser Leu Thr Cys Arg Ala Ser Gln Asp
        15                  20                  25

Ile Gly Ile Asn Leu His Trp Leu Gln Gln Glu Pro Asp Gly Thr Ile
        30                  35                  40

Lys Arg Leu Ile Tyr Ala Thr Ser Ser Leu Gly Ser Gly Val Pro Lys
45                  50                  55                  60

Arg Phe Ser Gly Ser Arg Ser Gly Ser Asp Tyr Ser Leu Thr Ile Ser
            65                  70                  75

Ser Leu Glu Ser Glu Asp Phe Val Ala Tyr Tyr Cys Leu Gln Tyr Ala
                80                  85                  90

Ser Ser Pro Tyr Thr Phe Gly Gly Thr Lys Leu Glu Ile Lys Arg
            95                 100                 105

Ala Asp Ala Ala Pro Thr Val Ser Ile Phe Pro Pro Ser Ser Lys Leu
        110                 115                 120

Gly
125
```

(2) INFORMATION FOR SEQ ID NO:3:

(i) SEQUENCE CHARACTERISTICS:
        (A) LENGTH: 461 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..459

(ix) FEATURE:
        (A) NAME/KEY: mat_peptide
        (B) LOCATION: 58

(xi) SEQUENCE DESCRIPTION: SEQ ID NO:3:

```
ATG GAA TGC AGC TGG GTC TTT CTC TTC CTC CTG TCA ATA ACT ACA GGT      48
Met Glu Cys Ser Trp Val Phe Leu Phe Leu Leu Ser Ile Thr Thr Gly
-19             -15                 -10                  -5

GTC CAC TCC CAG GCT TAT CTA CAG CAG TCT GGG GCT GAG CTG GTG AGG      96
Val His Ser Gln Ala Tyr Leu Gln Gln Ser Gly Ala Glu Leu Val Arg
            1               5                   10

TCT GGG GCC TCA GTG AAG ATG TCC TGC AAG GCT TCT GGC TAC ACA TTG     144
Ser Gly Ala Ser Val Lys Met Ser Cys Lys Ala Ser Gly Tyr Thr Leu
        15                  20                  25

ACC AGT TAC AAT ATG CAC TGG GTA AAG CAG ACA CCT GGA CAG GGC CTG     192
Thr Ser Tyr Asn Met His Trp Val Lys Gln Thr Pro Gly Gln Gly Leu
    30                  35                  40                  45

GAA TGG ATT GGA AAT ATT TTT CCT GGA AAT GGT GAT ACT TAC TAC AAT     240
Glu Trp Ile Gly Asn Ile Phe Pro Gly Asn Gly Asp Thr Tyr Tyr Asn
            50                  55                  60

CAG AAG TTT AAG GGC AAG GCC TCA TTG ACT GCA GAC ACA TCC TCC AGC     288
Gln Lys Phe Lys Gly Lys Ala Ser Leu Thr Ala Asp Thr Ser Ser Ser
        65                  70                  75

ACA GCC TAC ATG CAG ATC AGC AGC CTG ACA TCT GAA GAC TCT GCG GTC     336
Thr Ala Tyr Met Gln Ile Ser Ser Leu Thr Ser Glu Asp Ser Ala Val
    80                  85                  90
```

```
TAT TTC TGT GCA AGA GGG AAC TGG GAG GGT GCT CTG GAC TAC TGG GGT       384
Tyr Phe Cys Ala Arg Gly Asn Trp Glu Gly Ala Leu Asp Tyr Trp Gly
     95                  100                 105

CAA GGA ACC TCA GTC ACC GTC TCC TCA GCC AAA ACG ACA CCC CCA CCC       432
Gln Gly Thr Ser Val Thr Val Ser Ser Ala Lys Thr Thr Pro Pro Pro
110                 115                 120                 125

GTC TAT CCA CTG GTC CCT GGA AGC TTG GG                                461
Val Tyr Pro Leu Val Pro Gly Ser Leu
                130
```

(2) INFORMATION FOR SEQ ID NO:4:

(i) SEQUENCE CHARACTERISTICS:
        (A) LENGTH: 153 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Cys Ser Trp Val Phe Leu Phe Leu Leu Ser Ile Thr Thr Gly
-19             -15                 -10                 -5

Val His Ser Gln Ala Tyr Leu Gln Gln Ser Gly Ala Glu Leu Val Arg
             1               5              10

Ser Gly Ala Ser Val Lys Met Ser Cys Lys Ala Ser Gly Tyr Thr Leu
         15                 20                  25

Thr Ser Tyr Asn Met His Trp Val Lys Gln Thr Pro Gly Gln Gly Leu
 30              35                  40                      45

Glu Trp Ile Gly Asn Ile Phe Pro Gly Asn Gly Asp Thr Tyr Tyr Asn
             50                  55                      60

Gln Lys Phe Lys Gly Lys Ala Ser Leu Thr Ala Asp Thr Ser Ser Ser
             65              70                  75

Thr Ala Tyr Met Gln Ile Ser Ser Leu Thr Ser Glu Asp Ser Ala Val
             80              85                  90

Tyr Phe Cys Ala Arg Gly Asn Trp Glu Gly Ala Leu Asp Tyr Trp Gly
     95                 100                 105

Gln Gly Thr Ser Val Thr Val Ser Ser Ala Lys Thr Thr Pro Pro Pro
110                 115                 120                 125

Val Tyr Pro Leu Val Pro Gly Ser Leu
                130
```

METHODS OF DELAYING DEVELOPMENT OF HMFG-ASSOCIATED TUMORS USING ANTI-IDIOTYPE ANTIBODY 11D10

CROSS-REFERENCE TO RELATED APPLICATIONS

This application claims the benefit of provisional application No. 60/049,540, filed Jun. 13, 1997.

STATEMENT OF RIGHTS TO INVENTIONS MADE UNDER FEDERALLY SPONSORED RESEARCH

This research is sponsored by the following government grants: National Cancer Institute (NCI) Program Grant U01-CA-65748; National Institutes of Health NIH R01 CA-60000. The government may have certain rights in this invention.

TECHNICAL FIELD

This invention relates to uses of anti-idiotype antibodies. More particularly, it relates to methods of treatment using anti-idiotype antibody 11D10, in which administration of 11D10 delays IIMFG-associated tumor development.

BACKGROUND ART

In spite of extensive medical research and numerous advances, cancer remains the second leading cause of death in the United States. Breast cancer is the most common cause of cancer deaths in women with over 150,000 new cases diagnosed annually. While the traditional modes of therapy, such as surgery, radiotherapy and chemotherapy, are widely used and are in many instances successful, the still existing high death rate from cancers such as breast compels the need for alternative or additional modes of therapy.

Even if a patient responds to traditional modes of therapy, there is often a significant risk of recurrence of the disease. This is especially true if the disease has spread when diagnosed. Even after "successful" treatment, in which a remission is observed a patient can have high risk of recurrence, and can only "watch and wait." There are presently no further courses of action to delay or prevent recurrence.

One approach to cancer therapy has been immunotherapy. However, immunotherapy of human cancer using tumor cells or tumor-derived vaccines has been disappointing for several reasons. It has been consistently difficult to obtain large quantities or purified tumor-associated antigens which are often chemically ill-defined and difficult to purify. In addition, there remains the problem of immunobiological response potential against tumor antigens, or in other words, the question of whether a cancer patient can effectively mount an immune response against his or her tumor. Tumor-associated antigens (TAA) are often a part of "self" and usually evoke a very poor immune response in a tumor-bearing host due to tolerance to the antigens, such as T cell-mediated suppression. Moreover, cancer patients tend to be immunosuppressed and only respond to certain T-dependent antigens.

Immunobiologists have learned that a poor antigen (in terms of eliciting an immune response) can be turned into a strong antigen by changing the molecular environment. Changes of hapten carrier allow T cell helper cells to become active, making the overall immune response stronger. Thus, changing the carrier can also turn a tolerogenic antigen into an effective antigen. McBridge et al. (1986) Br. J. Cancer 53:707. Often the immunological status of a cancer patient is suppressed such that the patient is only able to respond to certain T-dependent antigens and not to other antigen forms. From these considerations, it would make sense to introduce molecular changes into the tumor associated antigens before using them as vaccines. Unfortunately, this is impossible to accomplish for most tumor antigens, because they are not well defined and are very hard to purify.

The network hypothesis of Lindemann ((1973) *Ann. Immunol* 124:171–184) and Jerne ((1974) *Ann. Immunol.* 125:373–389) offers an elegant approach to transform epitope structures into idiotypic determinants expressed on the surface of antibodies. According to the network concept, immunization with a given tumor-associated antigen will generate production of antibodies against this tumor-associated antigen, termed Ab1; this Ab1 is then used to generate a series of anti-idiotype antibodies against the Ab1, termed Ab2. Some of these Ab2 molecules can effectively mimic the three-dimensional structure of the tumor-associated antigen identified by the Ab1. These particular anti-idiotypes called Ab2β fit into the paratopes of Ab1, and express the internal image of the tumor-associated antigen. The Ab2β can induce specific immune responses similar to those induced by the original tumor-associated antigen and can, therefore, be used as surrogate tumor-associated antigens. Immunization with Ab2β can lead to the generation of anti-anti-idiotype antibodies (Ab3) that recognize the corresponding original tumor-associated antigen identified by Ab1. Because of this Ab1-like reactivity, the Ab3 is also called Ab1' to indicate that it might differ in its other idiotypes from Ab1.

A potentially promising approach to cancer treatment is immunotherapy employing anti-idiotype antibodies. In this form of therapy, an antibody mimicking an epitope of a tumor-associated protein is administered in an effort to stimulate the patient's immune system against the tumor, via the tumor-associated protein. WO 91/11465 describes methods of stimulating an immune response in a human against malignant cells or an infectious agent using primate anti-idiotype antibodies. However, not all anti-idiotype antibodies can be used in therapeutic regimens against tumors. First, only a fraction of antibodies raised against an Ab1 are limited in their reactivity to the paratope of Ab1 (i.e., are non-reactive against features shared with other potential antibodies in the host). Second, anti-idiotype antibodies are not necessarily immunogenic. Third, even if an anti-idiotype elicits an immune response, only a fraction of these immunogenic anti-idiotypes elicit an immune response against the tumor antigen and not against other antigens with less specificity. Moreover, since different cancers have widely varying molecular and clinical characteristics, it has been suggested that anti-idiotype therapy should be evaluated on a case by case basis, in terms of tumor origin and antigens expressed.

Anti-Id monoclonal antibodies structurally resembling tumor-associated antigens have been used as antigen substitutes in cancer patients. Herlyn et al. (1987) *Proc. Natl. Acad. Sci. U.S.A.* 84:8055–8059; Mittleman et al. (1992) *Proc. Natl. Acad Sci. U.S.A.* 89:466–470; Chatterjee et al. (1993) *Ann. N. Y. Acad Sci.* 690:376–278. All of these studies were conducted with patients having advanced disease. Based on the observed immune response in at least some of the patients, it has been proposed that the anti-Id provides a partial analog of the tumor-associated antigen in an immunogenic context.

Human milk fat globules (HMFG) are milk fat globules secreted into breast milk by the breast epithelial cell, and are composed of fat droplets enveloped by plasma membrane. As such, HMFG is a rich source of epithelial membrane-associated antigens. One antigen component of HMFG is a high molecular weight, membrane-associated mucin that is associated with breast and other cancers such as ovarian, lung, and pancreas. The mucin contains a protein with known amino acid sequences derived from the CDNA. Semipurified HIMFG is available in small quantities from several sources and can be used in serological assays. Peterson et al. (1990)*Hybridoma* 9:221–235. However, HMFG is extremely difficult to isolate and purify, and purified HMFG is not available for patient immunization or animal studies. Further, inasmuch as some of the epitopes on HMFG are shared by normal tissues, specifically by non-penetrating glycoproteins, immunization with intact HMFG molecule might trigger potentially harmful autoimmune reactions. An immune reaction against a tumor-associated epitope, on the other hand would be much more desirable.

A series of murine monoclonal antibodies (mAbs) that recognize components of HMFG have been described that are primarily associated with human breast carcinomas and not with most normal tissues. Chatterjee et al. (1993) *Ann. N. Y. Accid. Sci.* 690:376–377; Ceriani et al. (1983) *Somatic Cell Genet.* 9:415–427. Among these mAbs, MC-10 (BrE-1) is the most restricted and specific, reacting with a large molecular weight (MW, 400,000) mucin-like protein present at high density and on >80% breast cancer cells and minimally expressed on a few normal tissues, such as the epithelial lining of lung and kidney tubules. Ceriani et al. (1983); Ceriani et al. (1990) *Antibody Immunoconjugates and Radiopharmaceuticals* 3:1 81–198.

Recurrent breast cancer is not curable by standard therapies. Thus, new therapeutic approaches for this disease are needed. Even if a patient responds to traditional therapy, there is often a significant risk of recurrence. Thus, new therapeutic approaches for this disease are needed. The present invention overcomes the deficiencies in the prior art by providing a monoclonal anti-idiotype antibody (11D10) as an antigen (Ag) that elicits an immune response against HMFG.

All references cited herein are incorporated by reference in their entirety.

DISCLOSURE OF THE INVENTION

The present invention is directed to therapeutic uses of the anti-idiotype antibody 11D10.

Accordingly, one aspect of the invention is methods of delaying development of HMFG-associated tumors in an individual having a low tumor burden, particularly high risk individuals. These methods include administration of an effective amount of anti-idiotype antibody 11D10 to the individual. In another aspect, the invention further includes administration of 11D10 with an adjuvant.

In another aspect, methods are provided for treatment of an HMFG-associated tumor in an individual with a low tumor burden which entail administering an effective amount of 11D10 to the individual.

BRIEF DESCRIPTION OF THE DRAWINGS

FIG. 1 depicts the cDNA sequence (SEQ ID NO:1) and the amino acid sequence (SEQ ID NO:2) of the light chain variable region of 11D10 and adjoining residues. The CDRs and framework regions are indicated.

FIG. 2 depicts the CDNA sequence (SEQ ID NO:3); and the amino acid sequence (SEQ ID NO:4) of the heavy chain variable region of 11D10 and adjoining residues. The CDRs and framework regions are indicated.

FIGS. 3A and B depict the amino acid sequences of the CDR and framework regions of the light chain (FIG. 3A) and heavy chain (FIG. 3B) variable region of 11D10.

MODES FOR CARRYING OUT THE INVENTION

This invention is based upon an ability of 11D10 to generate an HMFG specific immune response in patients who are at high risk of recurrence of HMFG-associated disease. We believe that administration of 11D10 can reduce the risk of HMFG-associated tumor occurrence, particularly in high risk individuals in the adjuvant setting.

11D10 is a murine anti-idiotype (Id) antibody (Ab2) which induces a specific immune response against a distinct and specific epitope of human milk fat globule (HMFG), a tumor-associated antigen. The generation and characterization of 11D10 as well as the DNA sequences encoding the variable regions of 11D10 (light and heavy chains) has been described in commonly owned patent application no. 08/766,350. A hybridoma that produces 11D10 has been deposited with the American Type Culture Collection (ATCC), 10801 University Blvd., Manassas, Va., USA 20110-2209 on Jan. 17, 1996 under the provisions of the Budapest Treaty for the International Recognition of the Deposit of Microorganisms for the Purposes of Patent Procedure. It was accorded Accession Number HB12020.

In a previous Phase I clinical trial, 12 breast patients having advanced HMFG-associated disease (who had failed all previous therapy and still had high tumor burden) were administered 11D10. Chakraborty et al. (1997) *Proc. Am. Ass. Cancer Research.* 4139. Five of the 12 patients generated significant levels of specific anti-anti-Id (Ab3) antibodies that were capable of inhibiting binding of Ab2 to Ab1 or vice versa. This is especially significant, as many of these patients, either due to the nature of their previous treatment or their disease or both, are moderately to severely compromised, and often received 11D10 as a final option. Affinity purified Ab3 from 3 patients' sera bound specifically to the purified HMFG antigen and immunostained the breast cancer tissue sections. The isotype of the antibody (Ab3/Ab1') was predominantly IgG. Peripheral blood lymphocytes (PBL) isolated from $3/12$ immunized patients showed in vitro idiotype specific T cell proliferative responses. The results suggest that anti-ID 11D10 can induce both humoral and cellular immune responses in some advanced breast cancer patients who were heavily pre-treated. Toxicity was minimal with only mild erythema and induration at the injection site. However, all of these patients displayed normal disease progression.

Definitions

As used herein, the terms "11D10," "11D10 antibody" and "11D10 monoclonal anti-idiotype antibody" are used interchangeably to refer to an anti-idiotype antibody (Ab2) which contains an epitope that at least partially resembles a distinct and specific epitope of human milk fat globule (HMFG) primarily expressed in human breast tumor cells. The generation and characterization of 11D10 is described in commonly owned patent application Ser. No. 08/766,350. See also Mukerjee et al. (1992) *FASEB J.* A2059 (Abs. 6505); Murkerjee et al. (1992) *FASEB J.* A1713 (Abs. 7792); Charaborty et al. (1994) *Proc. Am. Assoc. for Ccncer Res.* 35:2963; Chakraborty et al. (1995) *Cancer Res.* 55:1525–1530; Bhattacharya-Chatterjee et al. (1994) *Antigen and Antibody Mole. Eng. Breast Cancer Diagnosis and*

*Treatment*, (Ceriani, ed.) 139–148. Different biological functions are associated with 11D10, including, but not limited to, binding to Ab1 (MC-10) and/or Ab3 and an ability to induce an immune response (humoral and/or cellular) against HMFG in mice, rabbits, monkeys, and humans with advanced HMFG-associated disease, particularly HMFG-associated tumors, as well as humans with a history of HMFG-associated disease but no detectable disease.

"HMFG" is an abbreviation for human milk fat globule. HMFG has several protcinaceous (and thus antigenic) components. As used herein, it refers to a semi-purified extract of an HMFG-expressing breast cancer cell line, as prepared by the method of Ceriani et al. ((1977) *Proc. Natl. Acad. Sci. USA* 74:582–586), along with antigenically related substances, including HMFG expressed on breast cancer cells and more highly purified preparations. Contained in HMFG is a high molecular weight mucin of known amino acid sequence, an epitope of which is recognized by the monoclonal antibody MC-10 used as Ab1 in raising 11D10. Accordingly, anti-HMFG immunological reactivity induced by immunizing an animal with 11D10 preferably binds a polypeptide epitope or an antigenic determinant related to that recognized by MC-10.

MC-10 was chosen for production of anti-Id because it defines a unique and specific epitope of a high molecular weight mucin of human milk fat globule (HMFG), primarily expressed at high density by human breast cancer and some other tumor cells but is not found on normal adult tissues by immunoperoxidasc staining, or hematopoictic cells including granulocytes by flow cytometry analysis. MC-10 (also called BrE1) is quite restricted and specific in the sense that it reacts with a large molecular weight (MW 400,000) mucin present in only minute amounts in human mammary epithelial cells and increased by at least 10-fold on breast carcinoma cells. WO 8907268; EP 401247. The antibody is cytotoxic for breast cancer cells in vitro studies. Ceriani et al. (1983); Peterson et al. (1990).

MC-10 has a very restricted histopathological distribution in normal tissues. MC-10 only binds some areas of the epithelial lining of the lung and scattered distal convoluted tubules of the kidney, with no apparent histopathological binding to normal breast and many other normal epithelia (colon, pancreas, stomach, thyroid, bladder, liver) and other normal tissues (adrenal, brain, lymph node, myocarditum, ovary, spleen, testis). On the other hand, a high percentage of different human tumors, including breast, endometrium, lung, ovary, and pancreas bind mAb MC-10 intensely. The formalin fixed tumors studied for MC-10 binding (number positive/total number) include: breast carcinoma (CA) (144/182), colon CA (3/27), duodenum CA (0/1), endometrium CA (7/14), kidney CA (0/11), lung CA (41/47). ovary CA (20/26), pancreas CA (9/15), prostate CA (0/2), salivary gland CA (0/3), stomach CA (2/7), thyroid CA (0/7), hepatocholangio CA (8/33), islet cell CA (0/2), lymphoma (0/20), melanoma (0/23), meningioma (0/5), Merkel cell CA (4/9), mesothelioma (1/11), neuroblastoma (0/2), oncocytoma (1/1), paraganglioma (0/10), plleoadenoma (0/7). Among the sarcomas: unclassified (0/1), alveolar (0/1), angiosarcoma (0/1). clear cell (0/2), cystosarcoma (0/1), epithelioid (5/12), Ewing's (0/1), fibrosarcoma (0/1), leiomyoma (0/2), liposarcoma (0/1), malignant fibrohistiocytoma (0/2), synovial mesothelioma (0/7), spindle cell CA (5/16), undifferentiated (1/9); schwannoma (0/3), seminoma (0/4), teratoma (0/3), thymoma (0/8), transitional CA (5/10), undifferentiated CA (7/29), Warthin's tumor (0/1). Ceriani et al. (1990). We have also studied hematopoetic cells for the presence of MC-10 antigen by FACS analysis in our laboratory and found those cells, including granulocytes and platelets, negative for antigen. The positive control MCF-7 cells stained heavily with MC-10.

A "HMFG-associated tumor" is one that contains an HMFG antigen, especially expressed on the tumor cell surface, that binds to MC-10 (Ab1). As noted above, this antigen is found on a wide variety of tumors particularly breast cancer (over 90% of breast cancer patients have tumors that react with MC-10). Thus, 11D10 has the potential to be used in a wide variety of cancers in which HMFG is detected. Methods of detecting HMFG are known in the art and examples are described herein.

As used herein, "treatment" is an approach for obtaining beneficial or desired results. For purposes of this invention, beneficial or desired results include, but are not limited to, one or more of the following: alleviation of symptoms, diminishment of extent of disease, stabilized (i.e., not worsening) state of disease, preventing spread (i.e., metastasis).of disease, preventing occurrence or recurrence of disease, delay or slowing of disease progression, amelioration of the disease state, and remission (whether partial or total). Also encompassed by "treatment" is a reduction of pathological consequences of a HMFG-associated tumor(s).

As used herein, "delaying" development of an HMFG-associated tumor(s) means to defer, hinder, slow, retard, stabilize, and/or postpone development of the disease. This delay can be of varying lengths of time, depending on the history of the disease and/or individual being treated. As is evident to one skilled in the art. a sufficient or significant delay can, in effect, encompass prevention, in that the individual does not develop the disease. A method that "delays" development of HMFG-associated tumor(s) is a method that reduces probability of disease development in a given time frame and/or reduces extent of the disease in a given time frame, when compared to not using the method. Such comparisons are typically based on clinical studies, using a statistically significant number of subjects.

"Development" of HMFG-associatcd tumor(s) means progression of the tumor(s). Tumor development can be detectable using standard clinical techniques as described herein. However, development also refers to disease progression that may be undetectable. For purposes of this invention, progression refers to the biological course of the disease state, in this case (i.e., IIMFG-associated tumors) cell division and/or metastasis of the HMFG-associated tumor. "Development" includes occurrence, recurrence, and onset. As used herein "onset" or "occurrence" of HMFG-associated disease includes initial onset and and/or recurrence.

As used herein, "low tumor burden" means that an individual does not have advanced HMFG-associated tumor (s). "Advanced" HMFG-associated tumor(s) means that there is detectable metastasis, that is, detectable tumor masses at sites other than the primary site of the tumor. Tumor masses are generally detected by imaging techniques known in the art such as X-ray, CT scan, or MRI, as well as imaging and diagnostic techniques that detect tumor masses that would be detected by X-ray, CT scan, or MRI. As used herein, "advanced" disease does not include lymph node involvement. It is understood that "low tumor burden" also includes no detectable tumor using convention diagnostic techniques such as X ray, CT scan, or MRI. Preferably, an individual with low tumor burden has been assessed as having stage III, preferably stage II, even more preferably stage I disease. As described below, also preferable is disease that has been treated by surgery, radiation and/or chemotherapy and is no longer detectable by conventional diagnostic and/or imaging techniques. As another preferred example, individuals with low "low tumor burden" also include those having surgical resection of the primary tumor in which no detectable disease or some disease remained due to, for example, inability to resect all detectable disease, or less extensive disease. Other examples of low tumor burden categories are provided below.

As used herein, a "high risk" individual is an individual who is at major risk of development of HMFG-associated tumors. A "high risk" individual may or may not have detectable disease, and may or may not have displayed detectable disease prior to the treatment methods described herein. "High risk" denotes that an individual has one or more so-called risk factors, which are measurable parameters that correlate with development of HMFG-associated tumors. An individual having one or more of these risk factors has a higher probability of developing HMFG-associated tumors than an individual without these risk factor(s). These risk factors include, but are not limited to, age, sex, race, diet, history of previous disease, presence of precursor disease, glenetic (i.e., hereditary) considerations, and environmental exposure. Examples (i.e., categories) of high-risk groups are discussed below.

Depending on the basis and context of assessment of high risk, the time frame within which probability of disease or tumor development, progression, and/or onset would more likely than not occur would vary. For instance, with breast cancer, high risk patients in the adjuvant setting, the risk of occurrence is typically measured within one to five years. For patients with non-small cell lung cancer in the adjuvant setting, the risk of occurrence is typically measured within one to two years. For patients who display precursor disease, the risk of occurrence can be measured in a longer time frame. For an individual who is considered high risk due to, for example, genetic or hereditary considerations, the risk of occurrence can be measured in an even longer time frame, including the expected lifetime of the individual.

An individual with "low risk" is one who is not considered "high risk".

"Adjuvant setting" refers to a setting in which an individual has had a history of HMFG-associated disease, particularly HMFG-associated tumors, and has been responsive to therapy. The prior therapy can have included, but is not limited to, surgical resection, radiotherapy, and chemotherapy. As a result of this prior therapy, these individuals have no clinically measurable tumor as detected by conventional diagnostic techniques such as X ray, CT scan, or MRI. or techniques that detect tumors detectable by X ray, CTF scan, or MRI. However, because of their history of HMFG-associated disease, these individuals are considered at risk of development of the disease. Treatment or administration in the "adjuvant setting" refers to a subsequent mode of treatment. The degree of risk (i.e., whether an individual in the adjuvant setting is considered "high risk" or "low risk") depends upon several factors, most usually the extent of disease when first treated.

As used herein, "adjuvant setting" is distinguished from an "adjuvant", which refers to a chemical or biological agent in a pharmaceutical preparation given in combination with an agent (such as an antibody, polynucleotide or polypeptide) to enhance its immunogenicity. Examples of adjuvants are described herein.

A "neo-adjuvant setting" refers to the period after diagnosis but before initiation of treatment modalities other than administration of 11D10. For example, if an individual is diagnosed as having a HMFG-associated tumor, such as breast, for which surgery is indicated, administration of 11D10 in a neo-adjuvant setting means that administration of 11D10 commences before surgery.

An "effective amount" is an amount sufficient to effect beneficial or desired results, preferably within a clinical setting. An effective amount can be administered in one or more administrations. For purposes of this invention, an effective amount of 11D10 is an amount of 11D10 that is sufficient to ameliorate, stabilize, or delay the development of the HMFG-associated disease state, particularly HMFG-associated tumors. Detection and measurement of these indicators of efficacy are discussed below.

An "individual" is a vertebrate, preferably mammal, more preferably human. Mammals include, but are not limited to, farm animals, sport animals, and pets.

Embodiments of the Invention

In one embodiment, the invention provides methods delaying development of an HMFG-associated tumor(s) in which an effective amount of 11D10 is administered to an individual having a low tumor burden. Examples of HMFG-associated tumors include, but are not limited to, breast carcinoma, ovarian carcinoma, non-small cell lung carcinoma, and pancreatic carcinoma. Methods of detecting HMFG-associated tumors are known in the art, including standard immunoassay and/or imaging techniques. As an example, HMFG-associated tumors can be detected by standard immunohistologic examination of affected tissue, using, for example, MC-10 as the primary antibody in an indirect immunofluorescence assay, FACS analysis, or immunoperoxidase staining assay.

In one embodiment, the invention encompasses administration of 11D10 to a high risk individual having a low tumor burden. As discussed above, a high risk individual displays one or more risk factors that correlate with HMFG-associated tumor development. High (i.e., increased) risk may be indicated, for example, on the basis of an individual's genotype (for example, presence of a gene(s) or mutations(s) that is associated with development of HMFG-associated tumors), increased expression of tumor-associated genes or decreased expression of tumor suppressor genes, presence of precursor disease (such as non-invasive masses), a family history of HMFG-associated cancer, a history of exposure to an environmental substance or form of radiation which is known or suspected of being carcinogenic or teratogenic (particularly suspected of causing HMFG-associated tumors), exposure to a potentially carcinogenic pathogen such as a retrovirus, or a history of other types of cancer or other types of abnormal or unregulated tissue growth. Also included as high risk are individuals suspected of having a HMFG positive tumor based on a positive test for anti-HMFG immunological reactivity. Such individual include those who may have had their primary tumor surgically removed and are at high risk because of the size of the primary tumor or the presence of positive lymph nodes.

Because all risk factors for developing HMFG-associated tumors are not known, and the interplay among these factors (in terms of overall risk) are not fully understood, it is clear to one skilled in the art that individuals suitable for administration of 11D10 for purposes of this invention can have features in common, and that individuals not falling clearly in the categories described above can nonetheless be considered suitable candidates for administration of 11D10. A skilled clinician can make an empirical determination whether an individual is suitable for 11D10 treatment. For example, an individual with a familial (i.e., genetic) history of breast cancer could be considered "high risk", even though no previous disease in this individual has been observed. In this context, administration of 11D10 to such an individual could result in delay of occurrence of disease, to the extent that the individual does not develop the disease within his or her lifetime (or develops it later than would have been expected). Another example is an individual who is being treated using traditional modes of therapy, and who is showing responsiveness to the therapy (i.e., remission). Such an individual may be adjudged as "high risk", even though the initial course of therapy is not yet completed, due to projection of progress by the administrator of the therapy, and can be a suitable candidate for receiving 11D10 before completion of the initial therapy. The discretion to determine whether treatment using 11D10 may be indicated is that of the person responsible for the therapy.

It is also evident that administration of 11D10 may be indicated even if an individual is not adjudged to be high risk (i.e., is "low risk") according to concurrent risk assessment criteria. For instance, an individual who has been successfully treated and is not considered high risk (due, for example, to the lack of detectable invasive disease at the time of diagnosis) may nonetheless be a candidate for receiving 11D10 as a precautionary measure, especially considering the lack of contraindications and lack of undesirable side effects so far observed from 11D10. Thus, the risk of disease progression may be lowered even further by administration of 11D10. As another example, an individual may believe that he or she is at risk of disease development, and may decide that receiving 11D10 would reduce this risk. Also suitable are individuals with supernormal levels of HMFG expression. Levels of HMFG expression can be determined by, for example, immunohistologic examination of affected tissue, using, for example, MC-10 as the primary antibody in an indirect immunofluorescence assay.

In another embodiment of the present invention, 11D10 is administered to a high risk individual in the adjuvant setting. Factors typical as indicating individuals of high risk in the adjuvant setting are invasion by the tumor into neighboring tissues (i.e.. extensive disease), and/or lymph node involvement. Examples of high risk individuals in the adjuvant setting include, but are not limited to, (a) patients with Stage II or Stage IIIA non-small lung cancer (NSCLC) who have had their tumor resected but have positive regional lymph nodes (these patients have a 60–80% relapse rate in the first 2 years); and (b) patients with breast cancer who have positive lymph nodes in preferably at least 5, more preferably at least 10 positive lymph nodes (70–80% relapse rate in the first 2 years for those with at least 10 positive lymph nodes). Another example of a high risk individual in the adjuvant setting is an individual having ovarian cancer which is an HMFG-associated tumor and has detectable disease post-surgery. This. post-surgery detectable disease, generally due to unresectable disease, is generally visually detected (for example, when a patient is in surgery), although its presence can be based on other methods of detection. such as CT scan.

In another embodiment, 11D10 is administered in a neo-adjuvant setting. It is understood that, for purposes of this invention, an individual in a neo-adjuvant setting has a low tumor burden. Preferably, when administered in the neo-adjuvant setting, an individual has low tumor mass.

Another example of an individual suitable for 11D10 therapy as described in this invention is an individual with low tumor burden. Thus, the present invention encompasses methods of treating HMFG-associated tumors in an individual having a low tumor burden comprising administering an effective amount of HMFG. As defined above, a "low" tumor burden means that the disease is not considered advanced. For example, a low tumor burden can be disease in partial or complete remission as adjudged by a clinical practitioner. "Low" tumor burden can also arise by a reduction of tumor burden of advanced disease such that the extent of disease is no longer considered advanced. Other examples of low tumor burden include disease contained to limited lymph node involvement. An individual with a low tumor burden can be further classified as "high risk" or "low risk," depending on the individual's history of disease and treatment. As one skilled in the art would readily appreciate, an individual with low tumor burden could be treated in the non-adjuvant, neo-adjuvant, and/or adjuvant setting(s).

The invention also includes methods of treatment using 11D10 for individuals having residual disease, particularly minimal residual disease. "Residual" disease is any 11D10-associated disease, particularly HMFG-associated tumor(s) remaining after therapy but which is undetectable by conventional diagnostic techniques such as X ray, CT scan, or MRI, or techniques that detect tumors detectable by X ray, CT scan or MRI. Thus, "residual disease" refers to the likely presence of disease that can develop into detectable disease, and refers to a prognosis and/or assumption made in an adjuvant setting. Depending on the type of HMFG-associated tumor and, for example, the extent of disease upon diagnosis, an individual can be adjudged to have residual disease, even though no detectable disease is present. For example, an individual with resectable NSCLC has residual disease after surgery (i.e., resection), even if an apparent complete remission has occurred. Similarly, an individual with breast cancer can have micrometastatic residual disease after chemotherapy. Alternatively, an individual who is currently undergoing therapy for an HMFG-associated tumor also has "residual" disease. It is understood that, as used herein, "residual" disease does not include advanced disease. "Residual" disease and "minimal residual" disease as used herein are both undetectable using conventional diagnostic techniques such as X ray, CT scan, or MRI, or techniques that detect tumors detectable by X ray CT scan or MRI, but refer to varying extent or degrees of the disease.

The invention also encompasses methods of reducing risk of occurrence of HMFG-associated disease, particularly HMFG-associated tumors. In these methods, an effective amount of 11D10 is administered to an individual at risk for developing HMFG-associated disease. "Reducing risk of occurrence" means that the risk of occurrence and/or reoccurrence of HMFG-associated disease is lower in individuals receiving 11D10 than those individuals (having the same risk of occurrence) who do not. An individual "at risk" for developing HMFG-associated disease can be high risk or low risk, depending on the clinical and genetic history and status of the individual.

In another embodiment, the invention provides methods of treating an HMFG-associated tumor, particularly breast cancer, which include administration of certain chemotherapeutic agents and 11D10. We believe that certain chemotherapeutic agents may act synergistically with 11D10 to enhance the immune response. Appropriate chemotherapeutic agents may be determined based on data indicating that the chemotherapeutic agent(s) may stimulate the immune response, or not diminish the immune response. Methods of measuring the immune response are known in the art and are described herein. Administration of these chemotherapeutic agents generally follow accepted clinical protocols.

For all of the above-described embodiments of the present invention, 11D10 can be prepared, administered, and monitored as described in the following sections.

Preparation and Administration of Anti-idiotype Antibody 11D10

All embodiments of this invention entail administration of an effective amount of 11D10.

11D10 can be obtained several ways. For example, 11D10 can be produced from the hybridoma ATCC No. HB 12020 described herein. Methods of antibody isolation are well known in the art. See, for example, Harlow and Lane (1988) *Antibodies: A Laboratory Manual*, Cold Spring Harbor Laboratory, New York, and Sambrook et al. (1989) *Molecular Cloning: A Laboratory Manual*, Cold Spring Harbor Laboratory. The antibody can be obtained from the hybridoma via tissue culture or from mouse ascites. These techniques are known in the art. For example, the cells can be cultured in a suitable medium, and spent medium can be used as an antibody source. Optionally, matrix-coated channels or beads and cell co-cultures may be included to enhance growth of antibody-producing cells. For the production of large amounts of antibody it is generally more convenient to obtain an ascites fluid. Such methods are known in the art, and generally comprise injecting hybridoma cells into an immunologically naive histocompatible or immunotolerant mammal, especially a mouse. The mammal is optionally primed for ascites production by prior administration of a suitable composition; for example, Pristane. Preferably, 11D10 is purified from BALB/c ascites using recombinant protein G-agarose chromatography followed by Protein-A-CL-sepharose 4B chromatography.

Alternatively, 11D10 can be chemically synthesized using techniques known in the art, for example, using a commercially available automated peptide synthesizer such as those manufactured by Applied Biosystems. Inc. (Foster City, Calif.).

11D10 can also be obtained by employing routine recombinant methods such as described in Sambrook et al. (1989). For instance, a polynucleotide encoding either the 11D10 heavy or light chain can be cloned into a suitable expression vector (which contains control sequences for transcription, such as a promoter). The expression vector is in turn introduced into a host cell. The host cell is grown under suitable conditions such that the polynucleotide is transcribed and translated into a protein. Heavy and light chains of 11D10 may be produced separately, and then combined by disulfide bond rearrangement. Alternatively, vectors with separate polynucleotides encoding each chain of 11D10, or a vector with a single polynucleotide encoding both chains as separate transcripts, may be transfected into a single host cell which may then produce and assemble the entire molecule. Preferably, the host cell is a higher eukaryotic cell that can provide the normal carbohydrate complement of the molecule. The 11D10 thus produced in the host cell can be purified using standard techniques in the art.

A polynucleotide encoding 11D10 for use in the production of 11D10 by any of these methods can in turn be obtained from the hybridoma producing 11D10, or be produced synthetically or recombinantly from the DNA sequences described in commonly owned patent application Ser. No. 08/766,350 using standard techniques in the art. FIG. 1 depicts the cDNA sequence of the light chain variable region of 11D10 (SEQ ID NO:1); FIG. 2 depicts the cDNA sequence of the heavy chain variable region of 11D10 (SEQ ID NO:3). The full sequences of the 11D10 light and heavy chain constant regions have not been determined, but are expected to be identical or substantially identical to those of other mouse immunoglobulin molecules. For the mouse kappa light chain constant region, four genetic allotypes encoding two protein allotypes have been published by Solin et al. (1993) *Immunogenetics* 37:401–407, which is hereby incorporated herein by reference. FIG. 1 of Solin et al. depicts mouse and rat immunoglobulin kappa chain gene sequences comparing the sequences within the kappa chain constant region for different strains and highlighting allotypic differences. Included are kappa chain constant region sequences for BALB/c, PL, SJL, and *M. spretus*. Other naturally occurring allotypes are possible. The mouse $\gamma_1$ heavy chain constant region DNA sequence from newborn mice has been published by Honjo et al. (1979) *Cell* 18:559–568, which is hereby incorporated herein by reference. FIG. 5 of Honjo et al. shows the germ-line DNA sequence, along with the encoded protein sequence. Shown in the line above is another protein sequence obtained from the mouse myeloma MOPC 21. Other naturally occurring, allotypes are possible.

Polynucleotides encoding 11D10 can also be derived from the amino acid sequence of 11D10, the variable regions of which are provided in FIG. 1 (light chain; SEQ ID NO:2) and FIG. 2 (heavy chain; SEQ ID NO:4). Given the amino acid sequence of 11D10, one of skill in the art can design polynucleotides encoding 11D10.

The 11D10 antibody isolated from hybridoma ATCC No. HB 12020 is of the IgG1 mouse subclass, and may be isolated by any technique suitable for immunoglobulins of this isotype. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin. 11D10 may also be purified on affinity columns comprising the MC-10 (BrE1) paratope; for example, in the form of a purified Ab1 or Ab3.

If 11D10 is to be administered to an individual, 11D10 is preferably at least 80% pure, more preferably at least 90% pure, even more preferably at least 95% pure, even more preferably at least 98% pure, as well as free of pyrogens and other contaminants. In this context, the percent purity is calculated as a weight percent of the total protein content of the preparation. A preparation of 11D10 for immunization is described in Example 1.

Preferably, 11D10 is administered with a pharmaceutically acceptable excipient. A pharmaceutically acceptable excipient is a relatively inert substance that facilitates administration of a pharmacologically effective substance. For example, an excipient can give form or consistency to the vaccine composition, or act as a diluent. Suitable excipients include but are not limited to stabilizing agents, wetting and emulsifying agents, salts for varying osmolarity, encapsulating agents, buffers, and skin penetration enhancers. Examples of pharmaceutically acceptable excipients are described in *Remington's Pharmaceutical Sciences* (Alfonso R. Gennaro, ed., 18th edition, 1990).

Preferably, 11D10 is used with an adjuvant which enhances presentation of 11D10 or otherwise enhances the immune response against 11D10. Suitable adjuvants include aluminum hydroxide, alum, QS-21 (U.S. Pat. No. 5,057, 540), DHEA (U.S. Pat. Nos. 5,407.684 and 5,077,284) and its derivatives (including salts) and precursors (e.g., DHEA-S), beta-2 microglobulin (WO 91/16924), muramyl dipeptides, muramyl tripeptides (U.S. Pat. No. 5,171,568), monophosphoryl lipid A (U.S. Pat. No. 4,436,728; WO 92/16231) and its derivatives (e.g., DETOX™), and BCG (U.S. Pat. No. 4,726,947). Other suitable adjuvants include, but are not limited to, aluminum salts, squalene mixtures (SAF-1), muramyl peptide, saponin derivatives, mycobacterium wall preparations, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873–875. For veterinary use and for production of antibodies in animals, mitogenic components of Freund's adjuvant can be used. The choice of an adjuvant will depend in part on the stability of the vaccine in the presence of the adjuvant, the route of administration, and the regulatory acceptability of the adjuvant, particularly when intended for human use. For instance, alum is approved by the United States Food and Drug Administration (FDA) for use as an adjuvant in humans. Preferably, alum-precipitated 11D10 is used. Preparation of aluminum hydroxide precipitated 11D10 is described in Example 1. Preferably, QS-21 (i.e., STIMULON™ QS-21, Acquila Biotech, Worcester, Mass.) or DETOX™ PC (Ribi Immunochem, Hamilton, Mont.) is used.

STIMULON™ QS-21, available from Acquila Biotech (formerly Cambridge Biotech Corp.), Worcester, Mass., is a component of the extract from the tree Quillaja saponaria Molina. The QS-21 molecule ($C_{92}H_{148}O_{46}$, M. W. 1990) consists of a triterpene glycoside with the general structure of a quillaic acid 3,28-O-his glycoside. It consists of two structural isomers designed V1 and V2 at a typical ratio of V 1:V2 of approximately 2:1. Preferably, 100 µg of STIMULON™ QS-21 is used per administration of 11D10.

DETOX™ PC, available commercially from Ribi Immunobiochem (Hamilton, Mont.) is a mixture of cell wall skeleton (CWS) from *Mycobacterium phlei* and Monophosphoryl Lipid A (MPL®) from *Salmonella minnesota* Re595 prepared as stable oil-in-water emulsion with squalane, Tween-80 saline, egg phsophatidylcholine and (α-tocopherol. The ration of CWS to MPL® in DETOX™ PC is 10:1 (w/w). Each vial contains 300 µg CWS, 30 µg MPL®, 4.5 mg squalane, 0.6 mg TWEEN 80, 1.8 mg egg phosphatidylcholine and 60 µg α-tocopherol. Recommended storage of DETOX™ PC is 2–8° C., and sterile water is used as a diluent. Preferably, 250 µg CWS and 25 µg MPL® is used per administration.

11D10 can be used in conjunction with other immunomodulators, such as, for example, interleukin 2 (IL-2), IL-4, IL-3, IL-12, GM-CSF, G-CSF, interferon and keyhole limpet hemocyanin (KLH).

11D10 can also be used in conjunction with other agents that serve to enhance and/or complement 11D10's effectiveness. Examples of such agents include, but are not limited to, peptides derived from HMFG or 11D10. Preferred HMFG and 11D10 peptides are those based on homology between 11D10 and HMFG.

Alternatively, 11D10 can be encapsulated in liposomes. Liposomes suitable for packaging polypeptides for delivery to cells are known in the art.

11D10 can be heat treated before administration and the heat treatment can be in the presence of adjuvant (as long as heat treatment does not compromise the activity of the adjuvant), for example, alum. If QS-21 is used, then the Ig portion of the adjuvant can be heated. Generally, DETOX™ PC is not heated. For instance, 11D10 can be heated at about 40° to 80° C., preferably 45° C. to 60 ° C., for a period about 5 minutes to 2 hours, preferably 15 minutes to 1 hour. Heat treatment is preferably at 45° C. for 30 minutes in a sterile vial in a water bath. The heat treatment can occur anytime before administration. Preferably, heat treatment is within 7 days of administration. Other heat treatment procedures can be used, as long as the desired activity of 11D10 is not significantly compromised. The heat-treated 11D10 is then administered as described herein.

For treatment using 11D10, an effective amount of 11D10 is administered to an individual parenterally, preferably intracutaneously or subcutaneously. Other routes of administration include, but arc not limited to, intramuscular and intradermal. If alum (or aluminum hydroxide) precipitated 11D10 is used, 11D10 preferably administered intracutaneously. If QS-21 or DETOX™ PC is used, 11D10 is preferably administered subcutaneously. Depending on the particular adjuvant used, a manufacturer may provide suggested routes of administration as well as suggested amounts of adjuvants to be used. 11D10 can also be administered indirectly, by treatment of cultured cells followed by introduction of these cultured cells into an individual. The routes of administration can also vary during a course of treatment. For example, an individual can receive 11D10 intravenously followed by interperitoneal administration.

The amount of 11D10 given to the individual will depend upon several factors, such as the condition of the individual, the weight of the individual, the nature of the disorder or disease being treated, the extent of disease, the route of administration, how many doses will be administered, and the desired objective. Preferably, the dose per administration will range from about 10 µg to 20 mg, preferably 200 µg to 15 mg, more preferably 500 µg to 10 mg, even more preferably 1 mg to about 4 mg, even more preferably 2 mg. Preferably, the dose is 2 mg of alum-precipitated 11D10, 2 mg of 11D10 with QS-21, or 2 mg of 11D10 with DETOX™ PC.

The interval between administrations of 11D10 can vary and will depend upon the disorder being treated and the responsiveness of the individual. The 11D10 is preferably administered first as a priming dose followed by at least one, preferably two, more preferably three, boosting doses. Further boosting doses may be given to enhance or rejuvenate the response on a periodic basis. 11D10 can be administered on a weekly, preferably biweekly, basis until a desired, measurable parameter is detected, such as elicitation of an immune response. Administration can then be continued on a less frequent basis, such as bimonthly or monthly, as appropriate. Timing of subsequent injections (i.e., a maintenance dose) will depend, inter alia, upon the condition and response of the individual being treated. Ab3 levels can be monitored, preferably by the diagnostic methods described herein, to determine when maintenance (booster) administrations should be given, which could generally be about every two to three months. In one embodiment, the initial series of administrations is given at biweekly intervals for a total of four injections, followed by monthly injections.

It is understood that for some situations the individual receiving 11D10 may be moderately to severely immunocompromised, either due to the nature of previous treatment, the disease itself, or both. Thus, the time required to mount an immune response and/or the number of injections of 11D10 and/or the amount of 11D10 per administration may vary. For example, an individual may require a longer time to elicit an immune response once 11D10 has been administered. In this case, it is recommended that the individual continue to be monitored for an immune response, even if no initial (i.e., within the first month) immune response has been detected. As another example, an individual may require more than the average number of injections to elicit an immune response. Alternatively, it may be desirable to have the intervals between injections longer than monthly, for example, in order to optimize the immune response, such as a T cell response. Mounting an immune response is considered to be at least partially indicative, preferably completely indicative, of the effectiveness of 11D10 in terms of obtaining beneficial or desired results and thus may be a useful indicator of determining effective amounts of 11D10.

One possible indication of effectiveness of administration of 11D10, or whether administration of 11D10 is indicated, is the density of HMFG on the tumor cells. This density can vary widely from individual to individual, and may vary over the course of administration of 11D10 and/or over the course of the disease. As used herein, "density" of HMFG can refer to either or both of the following: (a) the number of cells per total cells in a given biological sample that have HMFG on their surface; (b) the amount of HFMG on the surface of each cell. Density (a) is calculated by noting the number of cells in a sample that are stained or otherwise indicate that HMFG is present divided by the total number of cells. This density would be preferably greater than about 20%, more preferably greater than about 30%, more preferably greater than about 50%, even more preferably greater than about 70%, even more preferably greater than about 80%, most preferably greater than about 90%. Thus, the invention includes administration of HMFG to an individual having density of HMFG greater than about 20%, preferably greater than 30%, more preferably greater than 70%, even more preferably greater than about 80%, most preferably greater than about 90%.

Density (b) is indicated by the relative intensity of staining (or intensity of any measurement indicating the presence of HMFG) of cells in a sample from one individual relative to, for example, a sample from another individual. For this density, one skilled in the art can make an empirical determination of density. Density (b) is relative to normal tissues (i.e., cells lacking HMFG, or unaffected cells), so preferred ranges may be about 1.5 fold, preferably about 3 fold, more preferably about 10 fold higher expression over unaffected cells, as detected by immunohistochemical staining density. Unaffected cells could also be from the same individual.

This is not to say that individuals with lower densities, for example, less than about 50% are not indicated for administration of 11D10. While not wishing to be bound by a single theory, it is possible that administration of 11D10 could elicit a series of immuno-reactions that result in a more general response that is effective against an HMFG-associated tumor, such as a cytotoxic T cell response. A lower density, however, may indicate that additional therapies are desirable.

It is understood that density can also be used as an indicator of extent of disease and response to administration of 11D10. For example, a sample taken from an individual at the onset of 11D10 administration may exhibit about 80% density (i.e., about 80% of the cells exhibit HMFG). After receiving 11D10, a sample taken from the same location may exhibit only about 50% density, indicating that HMFG-expressing cells are being destroyed. Similarly, if the intensity of staining of a sample from an individual receiving 11D10 diminishes upon receiving 11D10, this indicates that HMFG-bearing tumor cells are being destroyed.

For the purpose of raising an immune response 11D10 may be administered in an unmodified form. It may sometimes be preferable to modify 11D10 to improve its immunogenicity. As used herein, "immunogenicity" refers to a capability to elicit a specific antibody or cellular immune response, or both. Methods of improving immunogenicity include, inter alia, crosslinking with agents such as gluteraldehyde or bifunctional couplers, or attachment to a polyvalent platform molecule. Immunogenicity may also be improved by coupling to a protein carrier, particularly one that comprises T cell epitopes.

Administration of 11D10 can occur alone or in conjunction with other forms of therapy, whether established or experimental. "In conjunction with" means 11D10 can be given concurrently with, prior to, or after other therapies. For instance, 11D10 can be used to complement surgery, radiotherapy, chemotherapy and/or other drug therapies, either concomitantly or serially with respect to other therapies. The sequence and timing of these administrations can be determined empirically and will depend on such variables as the disease being treated, the condition of the patient clinical history and indications, and/or responsiveness to various therapies. Such determinations are within the skill of the art. Use of 11D10 in conjunction with anti-idiotype antibody 3H1 has been discussed above.

Preferably, 11D10 is administered before administration of other, adjunct therapies, such as chemotherapy and/or radiation, if these adjunct therapies are being used. Preferably, 11D10 is administered 1 day, preferably 3 to 5 days, before the first course of chemotherapy and/or radiation therapy, and 1 day, preferably 3 to 5 days, prior to each cycle of chemotherapy and/or radiation therapy. This allows the individual more time to mount an immune response.

Administration of 11D10 can continue for various courses, depending on the individual and disease being treated. Preferably, administration of 11D10 is continued for as long as an individual is able to mount an immune response, whether humoral and/or cellular. Administration of 11D10 should be discontinued if the individual displays unacceptable adverse reactions that are associated with the administration of 11D10, and may or may not be continued if the individual displays progressive disease. Continuation of administration of 11D10 in the event of progressive disease depends at least in part on whether continued administration of 11D10 could supplement other indicated therapies.

Determining the Effects of Administration of 11D10

In order to determine the effect of administration with 11D10, an individual may be monitored for either an antibody (humoral) or cellular immune response against HMFG, or a combination thereof. The individual can also be monitored for disease progression.

To determine the level of HMFG antibody (Ab3) in a biological sample, for example, serum or plasma is obtained from the individual. The sample may optionally be enriched for immunoglobulin before the assay is conducted, although this is not usually required. If a mouse immunoglobulin (such as 11D10 ) is to be used as an assay reagent the sample is preferably pretreated to remove anti-mouse immunoglobulin activity. This may be performed, for example, by depletion on a mouse immunoglobulin column, or by mixing non-specific mouse immunoglobulin into the sample and removing any immunoprecipitate formed.

To conduct the assay, anti-HMFG that may be in the sample is contacted with a non-limiting amount of an antigenic equivalent of HMFG. This may be isolated HMFG, nitrocellulose with HMFG affixed by direct blotting or by transfer from a polyacrylamide gel, cells expressing HMFG (such as MCF-7 or SKBR3 cells which are human breast carcinoma cell lines), membrane preparations from such cells, or fixed tissue sections containing HMFG. Alternatively, an anti-idiotype, particularly 11D10, may be used.

Once the immune complex has formed, it is generally separated from uncomplexed HMFG analog, and the amount of complex present is determined. The complex may be separated, for example, by centrifugation to collect cells or an immunoprecipitate, or capture by a solid phase. The amount of complex present may be measured by providing the HMFG analog with a label either directly, or by incubating with a secondary reagent. Alternatively, a competition assay may be performed, in which the sample is first incubated with the HMFG analog, and then a non-limiting amount of a labeled anti-HMFG reagent is added which competes with the anti-HMFG which may be present in the sample. Suitable labels include radiolabels, enzyme labels, fluorescent labels, and chemiluminescent labels. A standard curve is constructed using solutions known to contain no anti-HMFG, and solutions with various relative concentrations of anti-HMFG, in place of the sample. The sample containing the unknown amount of anti-HMFG is generally assayed in parallel, and the relative amount of anti-HMFG contained therein is determined by comparison with the standard curve. A preferred assay for determining anti-HMFG levels using HMFG antibody is radioimmunoassay (Example 2).

The isotype of the anti-HMFG antibody may be determined by including in the immunoassay an isotype-specific reagent(s), either at the separation or the labeling stage. For example, anti-human IgG may be used to separate or detect antibody of the IgG class present in a clinical sample of human origin. Presence of specific anti-HMFG of the IgG class generally indicates a memory response. Presence of anti-HMFG of the IgM class generally indicates ongoing immunostimulation, such as may be due to the presence of an HMFG expressing tumor, or ongoing treatment with 11D10.

If desired, anti-HMFG antibody detected in a biological sample may be further characterized; for example, by competition with anti-MC-10 (Ab1) to determine whether they are specific for related epitopes on HMFG. Competition assays between Ab1 and Ab3 are described in Example 2.

Anti-HMFG antibody may also be tested to determine whether it is cytotoxic. Complement mediated cytotoxicity (CMC) is determined, for example, by using HMFG-expressing target cells (such as MCF-7 or SKBR-3) labeled with $^{51}$Cr. Labeling may be accomplished by incubating about $10^6$ cells with ~200 $\mu$Ci Na$_2$$^{51}$CrO$_4$ for 60 minutes at 37° C., followed by washing. The assay is conducted by incubating the antibody (or clinical sample containing the antibody) with the target cells. The opsonized cells are then washed and incubated with a source of complement; for example, guinea pig serum pre-adsorbed to remove intrinsic antibody activity. After a suitable incubation period at 37° C., release of $^{51}$Cr into the medium is determined and compared with that from unopsonized control cells. Release of $^{51}$Cr correlates with CMC activity.

Another way of characterizing the anti-HMFG antibody is by testing, its ability to participate in an ADCC response (Cheresh et al. (1986) *Cancer Res.* 46:5112–5118). Radiolabeled HMFG-expressing target cells are incubated with the anti-HMFG (in the form of heat-inactivated serum), and effector cells. Normal human peripheral blood mononuclear cells (PBMC) are suitable effector cells, and preferably are used at an effector:target ratio of about 100. After approximately 4 hours at 37° C., the proportion of released $^{51}$Cr is determined as a measure of ADCC activity.

The cellular immune response in a subject being administered 11D10 may be quantified by conducting standard functional assays for specific T cell activity.

One type of assay measures T cell proliferation. In this test, peripheral blood mononuclear cells (PBMC) are obtained from a whole blood sample collected from the treated individual. For experimental animals, spleen cells may also be used. T cells may be enriched, for example, by centrifugation on a gradient such as FICOLL™. The cells are then cultured in the presence of 11D10 or HMFG or (more usually) irradiated HMFG expressing cells at various concentrations. Preferably, the stimulator cells are autologous with the responder cells, particularly in terms of histocompatibility Class II antigens. Extent of proliferation is then measured (often in terms of $^3$H-thymidine incorporation) in comparison to unstimulated cells. T cell proliferative activity in high risk patients' sera is shown in Example 2.

Another type of assay measures T cell cytotoxicity. In this test, an enriched T-cell population is used to effect lysis of $^{51}$Cr-labeled HMFG expression target cells, prepared as described above. Preferably, the effector cells are autologous with the target cells, particularly in terms of histocompatibility Class I antigens. The T cell population may optionally be pre-stimulated with HMFG or a relevant cell line. The T cells are then combined at various ratios with about $10^4$ labeled target cells; for example, in wells of a microtiter plate. The plate is optionally centrifuged to initiate cell contact, and the cells are cultured together for 4–16 hours at 37° C. The percent specific release of $^{51}$Cr into the medium is measured in comparison with labeled targets cultured alone (negative control) and targets lysed with a detergent such as 0.1% TRITON™ X-100 (positive control).

Other relevant measurements to determine the effect of 11D10 administration include clinical tests as may be appropriate in determining the development (i.e., progression) of cancer of the suspected type, whether direct or indirect indications of disease progression. Such tests may include blood tests, mammography, radioscintigraphy, CT scan, and MRI. Any measurable variable that correlates with disease progression is suitable. Any other tumor-associated marker is suitable for monitoring the course of therapy, such as, for example, carcinoembryonic antigen (CEA), or CA-125.

The invention also includes use of 11D10 for preparation of a medicament for use in treatment of HMFG-associated tumors, especially in those individuals with low tumor burden.

The following Examples are provided to illustrate but not limit the invention.

EXAMPLES

Example 1

Production of 11D10 Anti-idiotype Antibody for Immunization

Murine monoclonal antibody MC-10 (recognizing a distinct epitope of HMFG) was used to immunize syngeneic BALB/c mice for the production of anti-idiotype antibody 11D10 (IgG1-κ) as described in commonly owned patent application Ser. No. 08/766,350. Immunization of BALB/c mice, hybridoma fusion and cloning, selection of anti-idiotype (Ab2) and production of ascites in bulk quantities in mice were done as previously described. The Ab2 anti-idiotype 11D10 (IgG1) was purified from ascites by affinity chromatography on protein A-CL Sepharose 4B column followed by DEAE-Sepharose ion-exchange chromatography. The purity of the isolated immunoglobulin (>95%) was determined by sodium dodecylsulfate polyacrylamide gel electrophoresis (SDS-PAGE) and high pressure liquid chromatography techniques. Sterility, pyrogenicity, polynucleotides, mycoplasma and adventitious virus contamination and retrovirus removal validation tests were done in accordance with the United States Food and Drug Administration guidelines.

For use of alum-precipitated 11D10, 1 ml of 2% Alu-Gel S (Serva Fine Biochem, Inc., Garden City, Long Island, N.Y.) is added to 5 mg aliquots of purified mAb anti-Id (11D10). The volume is then adjusted to 10.0 ml with D-PBS and the mixture incubated on a vortex for one hour at room temperature. The mixture is then centrifuged at 2000 rpm at 24° C. for 10 minutes. The amount of mAb bound in the gel layer is determined by measuring spectrophotometrically the amount of unbound antibody in the supernatant. The Alu-Gel precipitated antibody is stored at 4° C. until use. These procedures are performed aseptically in a laminar flow hood and the final product was sterile and clearly labeled as anti-Id 11D10 Alu-Gel and aliquoted into pyrogen-free, sterile glass vials.

For use with QS-21 or DETOX™ PC, 11D10 is vialed alone at 2 mg/ml into sterile, pyrogen-free vials.

Example 2

Use of 11D10 to Treat High Risk Individuals in the Adjuvant Setting

Selection of Patients

High risk patients with HMFG-positive tumors are selected for this study. These patients do not have advanced disease, i.e., do not have detectable metastases. Generally, patients have received adjuvant chemotherapy and/or radiation therapy for breast cancer, non-small cell lung cancer, or ovarian. Those patients usually receive 11D10 at completion of treatment (typically at least 4 weeks after completion of treatment). Patients on hormone therapy receive 11D10 concurrently with treatment. Thus far, 4 patients have accrued to this study. Baseline studies include complete physical examination, chest radiography, computer axial tomography examination of the abdomen, routine blood counts and chemistries.

Preparation of Ab2

11D10 is obtained and alum-precipitated or mixed with QS-21 or DETOX™ PC as described in Example 1. The final product is tested for sterility, pyrogenicity and general safety in guinea pigs before use. An Investigational New Drug Application was approved through the United States Food and Drug Administration (BB-IND 5745). Before administration, 11D10 is heat treated in the presence of adjuvant at 45° C. for 30 minutes in a water bath. If alum is the adjuvant, 11D10 is heat treated in the presence of alum. If QS-21 is the adjuvant, 11D10 may be heat treated alone before mixing with QS-21. If DETOX™ PC is the adjuvant, only 11D10 is heat treated.

Treatment Schedule

All patients receive 2 mg 11D10 with adjuvant. Patients enter one of three regimens: (a) 2 mg of aluminum hydroxide (alum) precipitated 11D10; (b) 2 mg of 11D10 mixed with 100 µg QS-21, (c) 2 mg of 11D10 mixed with DETOX™ (250 µg CWS+25 µg MPL®). For regimen (c), 1.08 ml of 11D10 solution is mixed with 0.12 ml DETOXT™ PC, and 1.0 ml is withdrawn for injection.

Injections are intracutaneous if aluminum hydroxide-precipitated 11D10 is used. Injections are subcutaneous if QS-21 or DETOX™ PC is used. Four injections are given every two weeks, followed by monthly injections for a total of 24 months as long as there is immunological response and no evidence of progressive disease. Patients are evaluated every 12 weeks. Patients are removed from this study if they demonstrate progressive disease.

Toxicity and Responses

Toxicity is monitored for each patient, including analysis of hematopoietic cells, renal function, and hepatic function. Patients are also monitored very closely for disease activity.

Assays for Humoral Immunity (a) Total anti-11D10 response

The development of humoral immunity induced by immunization with 11D10 is assessed by testing sera obtained from patients before therapy and after each treatment with the vaccine. The sera is initially tested for total human anti-murine-antibody responses including anti-iso/allo/and anti-anti-idiotype antibodies by sandwich radioimmunoassay as described by Khajaeli et al. (1988) J. Nat'l Cancer Inst. 80:937–942. Briefly, microtiter plates are coated with 11D10 and incubated with different dilutions of patients' sera. After washings, the antigen-antibody reaction was tagged using $^{125}$I-labeled anti-Id 11D10 in a homogeneous sandwich radioimmunoassay. Since 11D10 is injected as intact IgG1, patients are expected to mount human anti-mouse antibody responses.

(b) Specific Ab3 response to Ab2

Sera from immunized patients with positive HAMA responses are tested for the presence of anti-antiidiotypic antibodies as follows. Sera are preincubated with normal murine immunoglobulin to block human antibodies against isotype and allotypic determinants and then checked for the presence of anti-anti-Id (Ab3) by reaction with 11D10 coated onto microtiter plates by RIA. Unrelated Ab2 serves as a control. After washing, the antigen-antibody reaction is tagged using $^{125}$I-labeled 11D10 in a homogeneous sandwich RIA as described above. Pretreatment non-immune sera and sera from normal donors serve as controls.

If a positive reaction is obtained, the sera are checked for the ability to inhibit the binding of $^{125}$I-labeled Ab1 (MC-10) to Ab2 (11D10) on the plate by radioimmunoassay or vice versa (inhibition of radiolabeled Ab2 binding to Ab1 on the plate). These reactions are done in the presence of excess normal murine immunoglobulin to block human antibodies against isotopic and allotypic determinants.

(c) Binding of Ab3 to tumor antigen

To assess humoral immune responses directed against native target antigens, patients' Ab3 sera is tested for reactivity with cell lines known to express MC-10 antigen such as MCF-7 cells in an RIA and also by FACS analysis. MCF-7 cells are available from the ATCC. In addition, the sera are checked for reactivity against a solubilized semi-purified preparation of MC-10 antigen (i.e., HMFG) and coated onto microtiter plates. The antigen-antibody reaction is detected by using $^{125}$I-labeled anti-human Ig reagents. Pre-immune sera is used as a control. Unrelated antigen is also used in the assay. Isotype of human Ab3 sera binding of MC-10 antigen is determined by ELISA using anti-human isotype specific reagents.

(d) Epitope analysis of Ab3

To demonstrate that Ab3 generated in treated patients and Ab1 (MC-10) bind to the same antigenic determinant, inhibition of MC-10 binding to Ag positive tumor cell line or MC-10 antigen by Ab3 sera is checked by RIA. A fixed amount of radiolabeled MC-10 (~90,000 cpm) is co-incubated with different concentrations of patients' purified Ab3 or Ab1 preparations and MCF-7 cells.

Ab3 is purified from patients' sera as follows. Fifteen milliliters of hyperimmune serum are passed over an immunoadsorbent column consisting of immunizing anti-idiotype immunoglobulin (11D10) coupled to Sepharose 4B. Anti-anti-idiotypic antibodies (Ab3) bound to the column are deluted with 0.1 M glycine-hydrochloric acid buffer (pH 2.4). The eluted antibody is neutralized with 3M Tris, dialyzed against PBS, pH 7.2 and then passed over an immunoadsorbent column consisting of allotype matched normal mouse immunoglobulin coupled to Sepharose 4B to remove anti-isotopic and anti-allotypic reactivities. Antibody that passes through is concentrated and used as purified Ab3. The isotype of Ab3 is determined by ELISA using human anti-isotype specific reagents (Tago).

Inhibition curves obtained with Ab1 and Ab3 that are very similar at different dilutions indicates that the patient' Ab3 binds to the same antigenic epitope as Ab1 and therefore contains antibody molecules with Ab1 properties.

(e) Cytotoxic activities of Ab3

If Ab3 in patient' sera bind specifically to tumor cells, the ability of Ab3 to lyse these cell in conjunction with effector cells and/or complement is tested by standard ADCC (Cheresh et al. (1986)) or CMC assays, (Herlyn et al. (1981) *Int. J. Cancer* 27:769). However, cytotoxic activity of the Ab3 may be dependent on its isotype, IgG1 being effective in ADCC and IgG1, IgG2, IgG3 and IgM in CMC.

Patient' sera are tested for ability to mediate antibody dependent cellular cytotoxicity (ADCC). Cheresh et al. (1986). For this assay, cultured human MCF-7 cells (which express HMFG on the cell surface) are used as target cells and were labelled with $^{51}$Cr. Normal human peripheral blood mononuclear cells (PBMC) are used as effector cells. The ADCC assay is performed in the presence of heat inactivated patient's serum with an effector to target cell ratio or 100:1 for 4 hours, followed by measurement of amount of $^{51}$Cr released.

(f) Quantitation of the Ab3 and Ab1 response

The expression of anti-anti-Id antibody (Ab3) in the patient' sera is quantitated by RIA inhibition studies as follows. Briefly, microtiter plates are coated with MC-10 IgG1 (Ab1) and reacted with a fixed amount of $^{125}$I-labeled 11D10. A standard inhibition curve is generated using purified MC-10 IgG1 as inhibitors. Next, patients' sera depleted of anti-iso-allotypic activity at different dilutions is checked for its ability to inhibit the Ab1-Ab2 reaction and the amount of Ab1-like antibody in the sera is estimated from the standard inhibition curve. The induction of Ab3 response as well as duration is compared among different adjuvants. If there is no statistical difference between Ab3 responses or duration at a number of doses, the titer of specific anti-tumor response (Ab1') in the sera by ELISA assay is compared against semi-purified MC-10 antigen coated plates.

(g) In vitro studies

If circulating Ab1' is not detected in Ab3 positive patients' sera, that may indicate that they may be bound to patient' tumor cells, or to circulating tumor antigen or they are of low affinity. These patient' PBMC are stimulated in vitro with antigen or Ab2 for the induction of tumor specific antibody. For this, PBMC obtained from blood collected before therapy, every three months, one month after the last immunization, and three months after the last immunization is cultured with various concentrations of 11D10 or unrelated Ab2, or MC-10 antigen (10 μg to 100 ng) in a modified Mishell-Dutton culture. Culture supernatants are harvested and checked first for the production of specific human immunoglobulins by ELISA assay and for binding to insolubilized preparation of Ab2 by radioimmunoassay. In addition, the supernatants are tested for the content of idiotope bearing molecule by their ability to inhibit the reaction between the $^{125}$I-labeled MC-10 (Ab1) to 11D10. The supernatants are also checked for their reactivity with MC-10 Ag-positive MCF-7 cells and Ag-negative cells such as M21/P6 or MOLT-4 in a binding assay with $^{125}$I-labeled anti-human Ig reagents by RIA or ELISA assay (sensitivity>1 ng) for the evaluation of Ab1' antibody.

The specificity of the effect of 11D10 is monitored by incubating PBMC with unrelated Ab2 of the same isotype. Since only Ab3 positive patients will be included in this in vitro study, PBMC stimulated with 11D10 should secrete antibodies binding to 11D10 and serve as a positive control.

Assays for Cell-Mediated Immunity

The goal is to examine whether a specific T cell response to the tumor associated MC-10 antigen is generated in patients with HMFG-associated tumors, particularly breast cancer, following a series of immunizations with the anti-idiotype antibody 11D10 in alum or mixed with QS-21 or with DETOX™ PC. Immunization with the vaccine could result in the generation of antibodies which alone can block T cell function. Nevertheless, considering the importance of T cells in the anti-tumor response, particularly CTL, it is necessary to examine whether this immunologic function exists.

T cell-mediated immunity is checked by: 1) testing if a T cell response is present which targets MC-10 antigen on the tumor cells, and 2) testing whether this response increases with repeated immunizations. The analysis proceeds in two phases. The first phase is to determine whether T cells from all PBMC samples received can be specifically expanded following in vitro immunizations against the 11D10 anti-Id antibody. If this occurs, it is determined whether these T cells can lyse or release cytokines against autologous MC-10 antigen bearing breast tumor cells and/or allogeneic MC-10 antigen expressing cancer cells sharing a single class I HLA antigen in common with the autologous CTL.

All patients entered into the trial undergo phlebotomy to collect one unit of whole blood prior to the first immunization. PBMC are isolated by standard Ficoll-Hypaque separation and cryopreserved for all future studies. These PBMC provide 1) antigen presenting feeder cells for subsequent studies, and 2) serve as baseline for T cell responses. In addition, following each immunization, 60 ml of peripheral blood is drawn, Ficoll-Hypaque separated and cryopreserved for the determination of T cell responses.

The T cell responses studied are generation of specific cytotoxic and/or cytokine producing T cells and proliferation of the T cell cultures in response to the antigens. When available, lymph node biopsies are obtained from the patients to provide a source of tumor infiltrating lymphocytes (TIL). Similar studies are conducted where possible using TIL to determine if tumor biopsies become a source of MC-10 antigen specific cells. Khazaeli et al. (1988) *J. Natl. Cancer Inst.* 80:937–942; Cheresh et al. (1985) *Proc. Natl. Acad. Sci. U.S.A.* 82:515. Also, tumor biopsies provide a source of tumor cells to serve as critical autologous targets for cytotoxicity assays, cytokine production, and proliferation assays.

(a) In vitro functional activity of T cells

Ficoll-Hypaque separated PBMC ($1-3\times10^6$) is incubated in the presence of: IL-2 alone (10 Cetus units/ml), 0.1 to 100 μg/ml anti-Id 11D10 antibody or HMFG. The cell culture medium consists of Iscoves medium supplemented with 10% human AB serum, gentamycin, sodium pyruvate, non-essential amino acids, L-glutamine and 10 Cetus units/ml recombinant IL-2. Every seven days the cultures are stimulated with irradiated autologous PBL pre-sensitized with the appropriate antigen used by day 0. The methods of in vitro sensitization are similar to those recently described (Steven et al. (1995) *J Immunol.* 154:762). Beginning day 21 and repeated on a weekly basis, proliferating cells are assessed for cell surface phenotype and cytotoxic and cytokine producing potential. Initially, all T cells are tested for their ability to recognize and lyse in 4 hours $^{51}$Cr release assays autologous EBV cells alone and autologous EBV transfected B cells with the cDNA containing the sequence for the 11D10 anti-Id molecule. Cultures lysing 11D10 transfected autologous EBV cells >10% are further tested against the NK sensitive line K562, the LAK sensitive line Daudi, autologous tumor if available and other HLA matched and mismatched HMFG bearing breast tumor cells. In addition, GM-CSF is assayed to determine if there is specific release of cytokines in addition to or in place of specific cytotoxicity. Proliferation of the cultures to the agents is determined by increases in cell numbers following in vitro stimulations.

Survival Results

Survival data is calculated based on length of time a patient has no detectable disease (i.e., length of time until progression). This length of time is determined based on entry date into the study. An even more meaningful statistic is length of time of no detectable disease (or to progression) as measured from the date of the last treatment.

Initial Data From Study

The study described in this Example was initiated. This data represents results as of May, 1998, from a total of 14 patients enrolled in the study. Of the 14 patients, 11 are currently receiving 11D10. Of the 3 patients who are off the study, 2 were withdrawn after progressive disease (the other patient withdrew from the study). Six of the patients receive QS-21; 3 of the patients receive alum (adjuvant data for the remaining 2 patients was not available).

Of 10 patients tested for antibody response, all 10 showed production of Ab3. All 7 patients tested for T cell proliferation showed an increase over baseline upon administration of 11D10 antibody, with various patterns of levels subsequent to this initial increase.

Six patients have been on the study for over 300 days, with two of those patients on the study over 400 days. For the two patients who showed progressive disease, time to progression was 92 days for one patient and 119 days for the other patient (both of these patients were receiving QS-21). There have been no deaths.

Example 3

Use of 11D10 to Treat Individuals with Low Tumor Burden

An individual who has been diagnosed as having an HMFG-associated tumor, such as breast cancer, is assessed for extent of disease using standard diagnostic imaging techniques such as CT scan. If the assessment shows that the individual does not have advanced disease, preferably no lymph node involvement, then the individual is given 11D10 in the same regimen as in Example 2. The individual is monitored for an immune response (see Example 2) and for extent of disease. Treatment is continued as long as an immune response is maintained, even if the disease becomes undetectable by the methods described herein. Intervals between administration of 11D10 may increase (i.e., longer than monthly) as long as an immune response is maintained and disease does not appear to progress.

Example 4

Administration of 11D10 to an Individual at Risk for Developing HMFG-Associated Tumor or Having Residual Disease An individual who is adjudged to be at risk for developing HMFG-associated tumor due to, for example, family history of HMFG-associated tumors, is administered 11D10 bi-weekly (or as often as twice a week) until an immune response is observed (see Example 2). Upon elicitation of an immune response, the interval between 11D10 administrations is increased by one week for each administration until the immune response begins to decrease. The interval between administrations of 11D10 is then sequentially adjusted to the previous interval until the immune response remains constant (i.e., is no longer decreasing). Administration of 11D10 is maintained at that interval. The individual is monitored for disease development every one to two years.

As a more particular example of this procedure, a 33 year-old woman elects to begin administration of 11D10 based on her family history of HMFG-associated breast cancer (mother, grandmother, and aunt had developed the disease). Injections begin on a biweekly basis until an immune response is detected (usually one to four months). The next injection is given after one week. The following injections are given as follows: (a) after two weeks, then (b) after three weeks, then (c) after four weeks, then (d) after five weeks, then (e) after six weeks, then (f) after seven weeks, then (g) after eight weeks. Injections are maintained every two months while monitoring the immune response every month. If the immune response is constant, the injections are given as follows: (a) every 9 weeks, then (b) every 10 weeks, then (c) every 11 weeks, then (d) every 12 weeks. Injections are maintained every three months while monitoring the immune response. If the immune response is constant, the intervals between 11D10 injections are increased by one week until injections are given every 6 months. If the immune response declines, then the interval is shortened until the response is regained to its original level. The individual is maintained on 11D10 administrations during her lifetime. If HMFG-associated tumors develop, then other therapies may be administered in conjunction with, or in lieu of, 11D10.

As another particular example, an individual with HMFG-associated breast cancer has the tumor resected, and there is no known lymph node involvement. No disease is detectable after surgery. Administration of 11D10 commences and is adjusted as described above, and the individual is monitored for disease progression.

Example 5

Administration of 11D10 in the Neo-Adjuvant Setting

An individual who has been diagnosed with an HMFG-associated tumor, such as an HMFG-associated breast or ovarian cancer, is scheduled to obtain treatment such as surgery and/or chemotherapy. During the time between diagnosis and the initiation of treatment (i.e. while the patient is waiting for these treatment(s) to commence), 11D10 is administered as described in Example 2. Administration of 11D10 continues after commencement of these treatment(s) and after the course of these treatment(s). The interval between administration of 11D10 is adjusted to that the individual maintains an immune response.

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

What is claimed is:

1. A method of delaying development of a human milk fat globule (HMFG)-associated tumor in an individual having a low tumor burden of an HMFG-associated tumor, comprising administering to the individual an amount of anti-idiotype antibody 11D10 sufficient to delay development of said HMFG-associated tumor, wherein 11D10 is produced by a hybridoma cell line deposited at the American Type Culture Collection (ATCC) as Accession No. HB 12020, or progeny thereof, whereby development of said HMFG-associated tumor is delayed.

2. The method of claim 1, wherein the individual is high risk of development of an HMFG-associated tumor.

3. The method of claim 2, wherein the individual is in an adjuvant setting.

4. The method of claim 1, wherein 11D10 is administered with an adjuvant.

5. The method of claim 4, wherein the adjuvant is aluminum hydroxide.

6. The method of claim 1, wherein the HMFG-associated tumor is a breast tumor.

7. The method of claim 1, wherein 11D10 is administered in an amount of about 1 mg to about 4 mg.

8. The method of claim 1, wherein 11D10 is administered in an amount of about 2 mg.

9. The method of claim 1, wherein 11D10 is administered at weekly intervals.

10. The method of claim 1, wherein 11D10 is administered every two weeks.

11. The method of claim 1, wherein 11D10 is heat-treated prior to administration.

12. A method of treatment of a human milk fat globule (HMFG)-associated tumor in an individual with a low tumor burden of an HMFG-associated tumor, comprising administering to the individual an amount of anti-idiotype antibody 11D10 sufficient to treat said HMFG-associated tumor, wherein 11D10 is produced by a hybridoma cell line deposited at the American Type Culture Collection (ATCC) as Accession No. HB 12020, or progeny thereof, whereby said HMFG-associated tumor is treated.

13. The method of claim 12, wherein the individual is high risk of development of an HMFG-associated tumor.

14. The method of claim 13, wherein the individual is in an adjuvant setting.

15. The method of claim 12, wherein 11D10 is administered with an adjuvant.

16. The method of claim 15, wherein the adjuvant is aluminum hydroxide.

17. The method of claim 12, wherein the HMFG-associated tumor is a breast tumor.

18. The method of claim 12, wherein 11D10 is administered in an amount of about 1 mg to about 4 mg.

19. The method of claim 12, wherein 11D10 is administered in an amount of about 2 mg.

20. The method of claim 12, wherein 11D10 is administered at weekly intervals.

21. The method of claim 12, wherein 11D10 is administered every two weeks.

22. The method of claim 12, wherein 11D10 is heat-treated prior to administration.

23. The method of claim 1, wherein the antibody has light and heavy chain variable region amino acid sequences in SEQ ID NO:2 and SEQ ID NO:4, respectively.

24. The method of claim 12, wherein the antibody has light and heavy chain variable region amino acid sequences in SEQ ID NO:2 and SEQ ID NO:4, respectively.

* * * * *